(12) United States Patent
Wisnewski

(10) Patent No.: US 7,794,476 B2
(45) Date of Patent: Sep. 14, 2010

(54) IMPLANTS FORMED OF SHAPE MEMORY POLYMERIC MATERIAL FOR SPINAL FIXATION

(75) Inventor: Paul Wisnewski, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 946 days.

(21) Appl. No.: 10/637,738

(22) Filed: Aug. 8, 2003

(65) Prior Publication Data

US 2005/0033295 A1 Feb. 10, 2005

(51) Int. Cl.
*A61B 17/70* (2006.01)

(52) U.S. Cl. ............................ 606/246; 403/28
(58) Field of Classification Search ............... 606/61, 606/78, 54, 69, 86, 105; 403/28–30
See application file for complete search history.

(56) References Cited

U.S. PATENT DOCUMENTS

| | | | |
|---|---|---|---|
| 4,820,782 A | 4/1989 | Ueno | |
| 5,391,168 A | 2/1995 | Sanders et al. | |
| 5,395,374 A | 3/1995 | Miller et al. | |
| 5,445,140 A | 8/1995 | Tovey | |
| 5,450,842 A | 9/1995 | Tovey et al. | |
| 5,551,871 A * | 9/1996 | Besselink et al. | 433/5 |
| 5,562,663 A | 10/1996 | Wisnewski et al. | |
| 5,609,608 A | 3/1997 | Benett et al. | |
| 5,728,098 A | 3/1998 | Sherman et al. | |
| 5,762,630 A | 6/1998 | Bley et al. | |
| 5,765,682 A | 6/1998 | Bley et al. | |
| 5,797,911 A | 8/1998 | Sherman et al. | |
| 5,911,737 A | 6/1999 | Lee et al. | |
| 5,928,237 A | 7/1999 | Farris et al. | |
| 5,968,070 A | 10/1999 | Bley et al. | |
| 6,024,764 A | 2/2000 | Schroeppel | |
| 6,059,815 A | 5/2000 | Lee et al. | |
| 6,077,268 A | 6/2000 | Farris et al. | |
| 6,102,933 A | 8/2000 | Lee et al. | |
| 6,210,413 B1 | 4/2001 | Justis et al. | |
| 6,235,028 B1 | 5/2001 | Brumfield et al. | |
| 6,240,630 B1 | 6/2001 | Lee et al. | |

(Continued)

FOREIGN PATENT DOCUMENTS

EP 0 326 426 8/1989

(Continued)

OTHER PUBLICATIONS

Strikeman, Alexandra, "Technology Review—Innovation: Total Recall", Technology Review (http://www.technologyreview.com/magazine/jun01/innovation8.asp).

(Continued)

*Primary Examiner*—Eduardo C Robert
*Assistant Examiner*—David Comstock

(57) ABSTRACT

This invention relates to a orthopedic implant that comprises a shape memory polymeric material. The orthopedic implant can be fabricated or molded in a desired configuration selected to provide support or tension to bony structures. Examples of implantable devices include spinal rods, bone plates, and bone fixation cords. The orthopedic implant can be deformed to a second configuration different from the first configuration either prior to implantation or after implantation. When desired, the shape memory polymeric material can be induced to revert to it original molded configuration. This can compress the attached bony structure and/or promote arthrodesis.

50 Claims, 7 Drawing Sheets

U.S. PATENT DOCUMENTS

| | | |
|---|---|---|
| 6,241,691 B1 | 6/2001 | Ferrera et al. |
| 6,281,262 B1 | 8/2001 | Shikinami |
| 6,293,949 B1 | 9/2001 | Justis et al. |
| 6,296,643 B1 | 10/2001 | Hopf et al. |
| 6,299,613 B1 | 10/2001 | Ogilvie et al. |
| 6,388,043 B1 | 5/2002 | Langer et al. |
| 2002/0013586 A1 | 1/2002 | Sherman et al. |
| 2003/0055198 A1 | 3/2003 | Langer et al. |
| 2004/0215192 A1 | 10/2004 | Justis et al. |

FOREIGN PATENT DOCUMENTS

| | | |
|---|---|---|
| EP | 0 470 660 A | 2/1992 |
| EP | 0 564 046 A | 10/1993 |
| EP | 0470660 B1 | 7/1995 |
| EP | 1 000 958 A1 | 5/2000 |

OTHER PUBLICATIONS

Japanese Patent Office, Japanese Office Action, Dec. 22, 2009.

* cited by examiner

IMPLANTS FORMED OF SHAPE MEMORY POLYMERIC MATERIAL FOR SPINAL FIXATION

BACKGROUND OF THE INVENTION

In general, the present invention relates to orthopedic implants and methods for treatment of spinal defects. More specifically, the present invention is directed to an implant, an assembly, or a system including the implant, and a treatment method using the implants and assemblies for spinal fixation.

Currently many people suffer from debilitating spinal defects including, but not restricted to, spondylitis, lordosis, scoliosis, kyphosis, and ruptured discs. These defects often require surgical intervention to relieve pain and restore the patient to a relatively normal activity level. The surgical treatment often entails restoring and stabilizing the patient's spinal alignment and maintaining a desired disc space height between adjacent vertebrae. Often one or more of the individual vertebrae must be stabilized and/or affixed into a desired position relative to adjacent vertebrae. For example, the spinal column can be forced into the desired alignment during surgery. After the spinal column has been aligned, one or more spinal rods, plates, and the like, which have been pre-configured as desired, are attached to the vertebrae to hold the spinal column in the desired configuration. The treatment can be combined with a full or partial discectomy, disc replacement, spinal fusion, and/or implantation of one or more spinal spacers into the disc space. The resulting assembly of spinal rods and/or plates should be sufficiently rigid to maintain the spinal alignment for an extended period of time, perhaps indefinitely.

During a patient's normal activity, biomechanical forces on the spine tend to force the spinal column to revert to its original alignment or to adopt an alternative configuration. The connections securing the rods to the bone fasteners can slip either during or after surgery. The rods can be difficult to adjust and properly align to create the desired effect and force on the spine. Further, the rods and connectors extend or stand out apart from the vertebrae and can impinge upon and irritate adjacent tissue/organs. All these problems can thwart the surgeon's original intention of eliminating the patient's pain and restoring a patient's normal spinal configuration and load bearing ability.

There is therefore a need remaining in the relevant art for improved implants and systems for treating spinal defects. The present invention is such an improvement and provides a variety of additional benefits and advantages.

SUMMARY OF THE INVENTION

The present invention relates to orthopedic implants, systems incorporating the implants, and the manufacture and use thereof. Various aspects of the invention are novel, nonobvious, and provide various advantages. While the actual nature of the invention covered herein can only be determined with reference to the claims appended hereto, certain forms and features, which are characteristic of the preferred embodiments disclosed herein, are described briefly as follows.

In one form, the present invention provides a system for treating a spinal defect. The system comprises: a rod member including an elongate body provided in a first configuration sufficient to extend from a first vertebra to a second vertebra, wherein the elongate body comprises a shape memory polymeric material; a first fixation device connected to the rod member; and a second fixation device connected to the rod member and spaced axially from the first fixation device, whereby the elongate body upon absorption of energy deforms to a second configuration different from the first configuration.

In another form, the present invention provides a connector for securing a rod member. The connector comprises: a body having a recess therein configured to receive a portion of the rod member; and a collar provided to at least partially encircle a portion of the rod member and sized to be received within the recess of the body, the collar comprising a shape memory polymeric material and provided in a first configuration whereby absorption of energy the collar deforms to a second configuration to secure the rod member to the body.

In yet another form, the present invention provides an orthopedic implant for treating a spinal defect. The implant comprises: a flexible cord provided in a first configuration sufficient to extend from a first bony structure to a second bony structure, wherein the cord comprises a shape memory polymeric material and upon absorption of energy the cord deforms to a second configuration different from the first configuration.

In yet another form, the present invention provides a method of treating a spinal defect. The method comprises: surgically preparing two or more vertebrae to receive a vertebral implant in a patient in need of treatment; connecting an elongate member to a first one of the two or more vertebrae, and connecting the elongate member to a second one of the two or more vertebrae, wherein the elongate member comprises a shape memory polymeric material and is provided in a first configuration; and stimulating the implant to induce said implant to deform into a second configuration.

In still yet another form, the present invention provides a method of treating a spinal defect. The method comprises: surgically preparing the patent to receive an implant; selecting an implant that comprises a flexible cord having a first length sufficient to extend from a first vertebra to a second vertebra, wherein the cord is formed of a shape memory polymeric material, attaching said cord to a first vertebra and then to a second vertebra, and stimulating the cord to absorb energy and induce the cord to deform.

Further objects, features, aspects, forms, advantages, and benefits shall become apparent from the description and drawings contained herein.

DETAILED DESCRIPTION OF THE INVENTION

Figure 1:
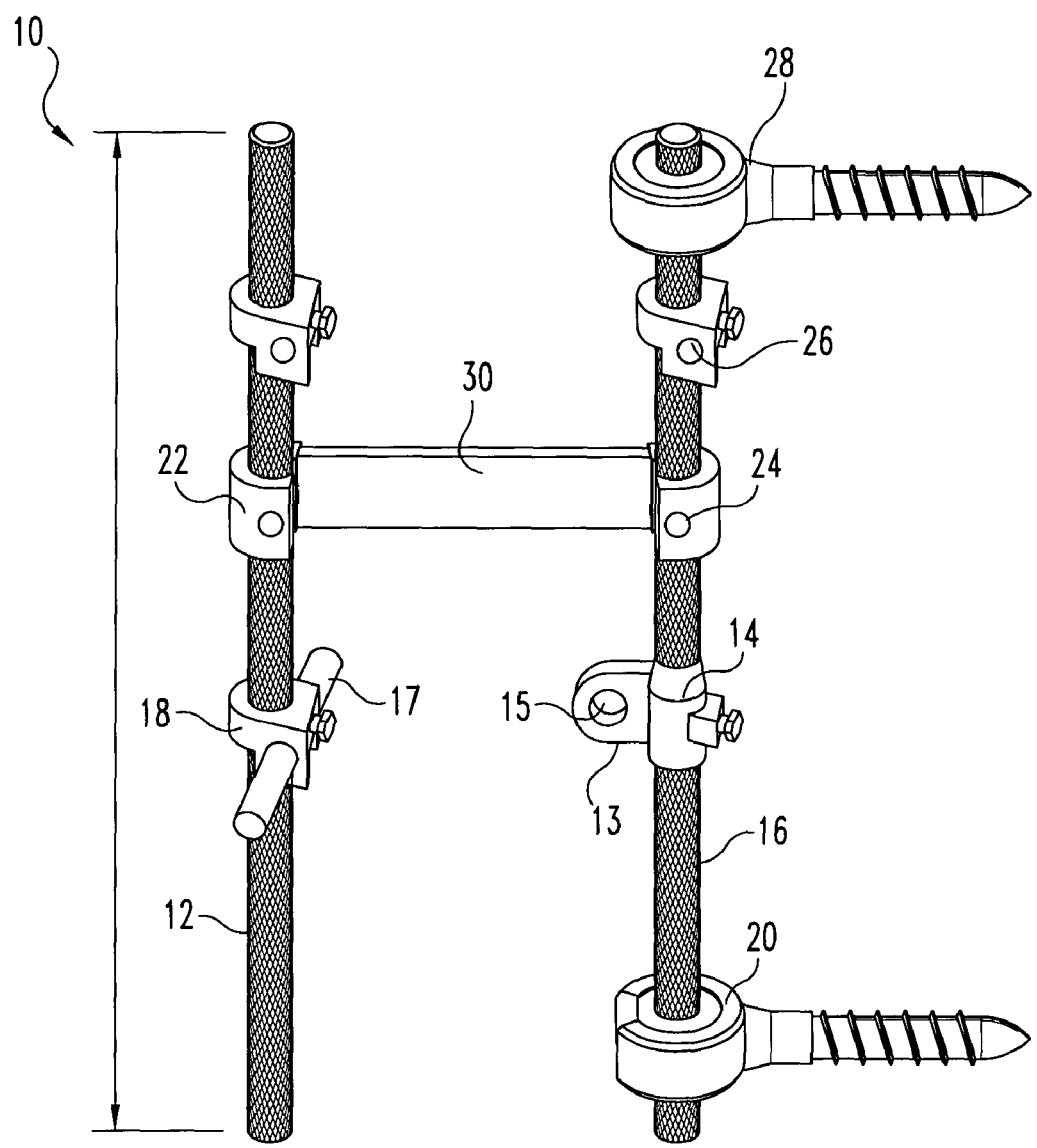
FIG. 1 is a perspective view of a pair of spinal rods formed of a shape memory polymeric material according to the present invention.

For the purposes of promoting an understanding of the principles of the invention, reference will now be made to the embodiments illustrated herein, and specific language will be used to describe the same. It will nevertheless be understood that no limitation of the scope of the invention is thereby intended. Any alterations and further modifications in the described devices assemblies and systems, and any further applications of the principles of the invention as described herein, are contemplated as would normally occur to one skilled in the art to which the invention relates.

In general, this invention provides implantable orthopedic devices and assemblies including the devices to treat spinal defects. The devices comprise a shape memory polymer (SMP) material. The devices can be readily deformed, as desired, to promote treatment of the spinal defect. In one form, the devices include a spinal fixation implant formed of a shape memory polymer. In another form, the devices include one or more connectors formed to include a shape memory polymeric material. In still yet other forms, the present invention provides systems and/or assemblies including one or more of the fixation implants and/or connectors for the treatment of spinal defects. The devices according to the present invention comprise a shape memory polymeric material. The SMP material imparts particular advantageous properties to the devices. The SMP material can be molded into a desired implant shape. The physical properties of the SMP material allows the implant to be rigid or non-deforming below a certain temperature. However, when the SMP material is heated, the implant becomes sufficiently plastic to be readily shaped and re-shaped, by hand if desired. Additionally, the SMP material exhibits the unique property of automatically reverting to its original, molded shape when the material is heated to a certain temperature level. This temperature level is termed the deformation temperature ($T_d$). Different SMP materials have different $T_d$.

The implantable devices of the present invention can be molded into a wide variety of sizes and configurations. The sizes and configurations can be selected to elicit a response or impose a constraint on a selected section of the spinal column or other bony structure. For example, the device can be sized to maintain the desired disc space height between the different vertebral bodies, including cervical, thoracic, lumbar, and sacral vertebral bodies. Alternatively, the device can be configured to restore a desired curvature or aligning force on a section of the spinal column. In other embodiments, the implantable device can be designed to exert tension on bone structures much like a ligament; such devices include plates, rods, cords, braids, and the like. The device can be molded to specific dimensions, for example, to a specific length to correct the bone defect.

The implantable device according to the present invention can then be shaped and/or deformed into a first, deformed configuration. The deformed spacer can be readily implanted. If desired, once implanted the device can once again be heated to a temperature level greater than its $T_d$ to facilitate treatment and/or bone fixation. Above $T_d$, the SMP exhibits superelasticity, and the device can revert to its original configuration or an approximation thereof.

Prior to implantation, the device can be deformed. It can be stretched so that its length is greater than its molded length. This would allow the surgeon to attach the device to distended bone structures. After implantation, and preferably after attachment to bone structures, the implanted device can be heated and allowed to revert to or approximate its molded dimension. The implanted device can thus serve to exert tension on bone structures, urging them closer together.

In other embodiments, the implantable device can be designed to support or separate bony structures. Examples of these devices include: a spinal rod, a cross member between two spinal rods, a spacer, an offset connector, and the like. These devices can be molded to a specific configuration or dimension. Prior to implantation, the device can be shaped or deformed to shorten its length, decrease its height, change its thickness, or modify its other dimensions, as desired. After implantation and attachment to the bony structures, the implanted device can be heated and allowed to revert to approximate its molded configuration/dimension. The implanted device can either add support to existing bone structures or distract and separate the bone structures.

Specific embodiments of the invention are illustrated by the following figures.

FIG. 1 illustrates a spinal fixation assembly 10 in accordance with the present invention. Assembly 10 includes a pair of elongate members, referred to here as spinal rods 12 and 16. A cross connector or lateral member 30 interconnects rods 12 and 16. A plurality of connectors 14, 18, 20, 22, 24, 26, and 28 are attached to one or more of the rods 12, 16. In one form, the spinal fixation assembly includes connectors such as bone screws illustrated as connectors 20 and 28 for securing at least one end of the rod 12 to a portion of bone. In other forms, the assembly includes connectors such as the interconnection members 22 and 24 to interconnect lateral member 30 to one or more of rods 12 and 16. Interconnection members 22 and 24 can be integral with lateral member 30 or separate from member 30.

Connector 14 includes an offset body 13 with an opening 15 through which another rod or fixation device can be inserted. Connector 18 is illustrated as an offset connector that can connect to another rod or support 17. Various other connectors, cross-linking devices, or fixation devices can be secured to rod 17 as desired.

Spinal rods 12, 16 are illustrated as substantially straight rods without any bends or exhibiting any curvature. It will be understood that rods 12, 16 can be provided in a variety of configurations, including rods, having a variety of cross-sectional configurations including round, square, rectangular, oval, and the like. One or more of rods 12, 16, lateral member 30, and connectors 14, 18, 20, 22, 24, 26, and 28 can but are not required to include or are formed of an SMP material. For example, each of these connectors can include a collar formed of an SMP material discussed more fully below. Other components of system 10 can be formed of a physiologically acceptable material such as stainless steel, titanium, titanium alloys (Ti-6Al-4V), ceramics, Co—Cr composite materials, and combinations thereof.

In other embodiments, one or more of the spinal rod(s) can be bent, deformed, or sized differently. The bends or curvature along rod(s) 12 and/or 16 can approximate the curvature of a portion of the patient's spinal column. Alternatively, rod(s) 12 and/or 16 can be bent to not conform to a portion of the patient's spinal column. Rather, one or more of rods 12 and 16 can be shaped to exert a force or urge one or more vertebral bodies into a desired placement to either restore disc space height or a desired alignment.

The following discussion refers specifically to spinal rod 12. However, it is to be understood that this discussion applies equally to spinal rod 16 or cross member 30. Rod 12 can be used by itself and attached to a bony structure using any known or commonly-used bone fasteners. Alternatively, rods 12 can be combined with one or more of rod 12, cross member 30, and connectors 14, 18, 20, 22, 26, and 28.

In one form, rod 12 can comprise a shape memory polymeric material. Consequently in this form, rod 12 exhibits unique properties. For example, rod 12 can be provided in an original configuration. In preferred embodiments, the original configuration is provided to correct a spinal defect. The rod 12 can be heated above a deformation temperature. Above the deformation temperature, the shape memory polymeric material becomes elastic or super-elastic and can be deformed, for example, by stretching, compressing, or bending. If spinal rod 12 is maintained or constrained in the deformed configuration and then cooled below the deformation temperature, $T_d$, it freezes in or retains that deformed configuration. The compressing or deforming force can be removed, and rod 12 will retain the deformed configuration until it is once again heated above $T_d$.

In a preferred embodiment, rod 12 is provided in a desired length illustrated by reference line 32. In one embodiment, the desired length is sufficient to attach to two adjacent vertebrae. In other embodiments, rod 12 can be provided in lengths ranging between about 1 mm and 50 mm, more preferably rod 12 is provided to have a length between about 2 mm and 300 mm. In still other preferred embodiments, rod 12 is provided with a cross-sectional dimension suitable to provide the requisite strength needed to withstand the biomechanical loading exerted by the spine, including one or more of strain, torsional, or compressive force(s). Rod 12 can have a cross-sectional diameter measured transverse to its length between about 2 mm and about 10 mm.

In the illustrated embodiment, rod 12 is an imperforate rod. In other embodiments, it will be understood that rod 12 can include one or a plurality of openings extending therethrough transverse to its longitudinal length. The openings extending through the elongate member rod can be provided to receive a connector or a bone fastener.

Rod 12 can be combined with other components to treat spinal defects. Such components include bone fasteners, connectors, connecting rods, spacers, and the like. Non limiting examples of additional components for use in the present invention include those found commercially in instrument systems sold by Medtronic Sofamor Danek under the trade names TSRH®, CD Horizon™, Vertex™ cervical rod system, and Paragon™, as well as those disclosed and described in U.S. Pat. Nos. 5,797,911, 6,077,268, and 6,210,413, which are all incorporated by reference herein.

Figure 2:
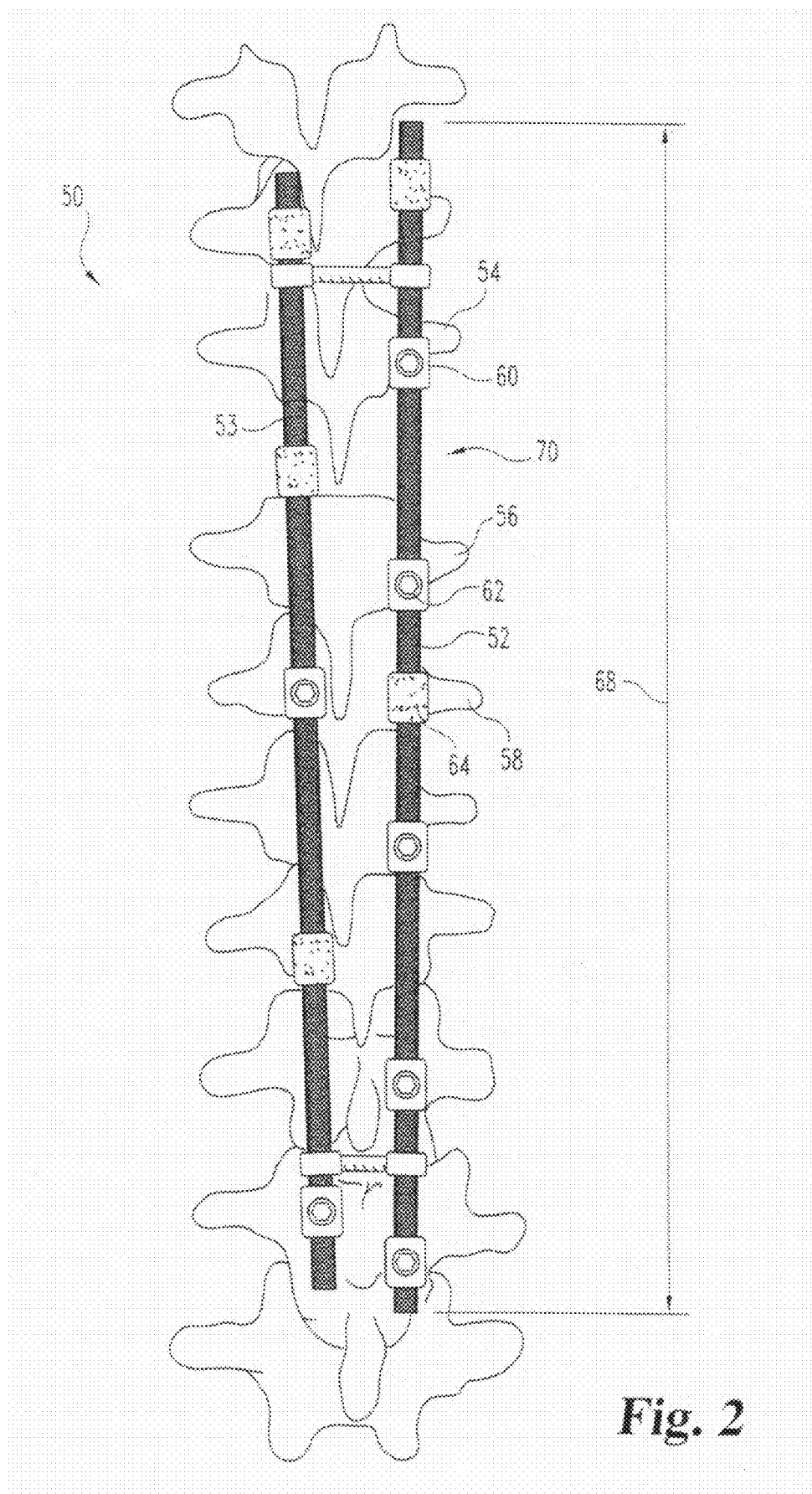
FIG. 2 is a perspective view of a pair of spinal rods formed of a shape memory polymeric material secured to a plurality of vertebral bodies in accordance with the present invention.

In use, a patient in need of surgical intervention is identified and prepared to receive the spinal implant/assembly. The patient is surgically prepared to receive the spinal implant either from a posterior, lateral, or anterior approach or a variation thereof as deemed medically expedient. Rod 12 can be provided to the surgeon by the manufacturer either in its original configuration or in a deformed configuration. Immediately prior to or during surgery, the surgeon can, if desired, deform rod 12 into a first configuration. Rod 12 can be repeatedly deformed until the desired configuration is obtained. Rod 12 can be heated by absorbing energy from a variety of sources, including a warm water or saline bath, infrared energy, microwave energy, and the like. The first configuration can be a stretched, lengthened rod compared to the original, molded configuration. Alternatively, the first configuration can be a compressed or shortened rod and/or bent as desired by the surgeon for the particular application or effect. After the surgeon has deformed rod 12 as desired, the temperature level of the shape memory polymeric material is then lowered below $T_d$. This effectively freezes the rod 12 into the deformed configuration. The surgeon can then implant rod 12 in its first deformed configuration into the patient. Preferably, the rod is secured to one or more bony structures. In this embodiment, rod 12 can be secured to one or more vertebral bodies using a bone hook or pedicle screw. FIG. 2 is a perspective view of one embodiment of an implant assembly 50 including spinal rods 52 and 53 extending across three adjacent lumbar vertebrae 54, 56, and 58. The following discussion will be directed toward rod 52, with the understanding that features and properties discussed can apply equally to rod 53. In the illustrated embodiment, spinal rod 52 is positioned posteriorly between the spinous process and the pedicle of each lumbar vertebra 54, 56, and 58. Bone fasteners 60, 62, and 64 secure rod 52 to vertebrae 54, 56, and 58, respectively. It will be understood by those skilled in the art that spinal rod 52 can be placed or attached to the vertebrae from any side, including posteriorly, anteriorly, and/or laterally, and with any means including bone nails, staples, bone adhesive, bone screws, bone hooks, , and the like. Spinal rod 52 in FIG. 2 is illustrated in its first configuration; that is, spinal rod 52 has been deformed or stretched and in this embodiment, rod 52 is significantly longer its original, molded configuration measured longitudinally as illustrated by reference 68.

It will also be observed that vertebra 54 is spaced from vertebra 56 demonstrating one example of a spinal defect. The disc space 70 is greater than desired. This spacing can be a result of spinal injury, disease, or a surgical intervention. For example, during surgery, the surgeon can distract the adjacent vertebrae to perform a full or partial discectomy, providing sufficient clearance to insert a spacer or a replacement disc. Regardless of the cause for the abnormally large spacing, it is desired to restore and maintain a normal disc space height. Once spinal rod 52 has been surgically implanted and connected to the desired vertebra, spinal rod 52 can be heated to a temperature level greater than $T_d$ of the particular shape memory polymeric material. The resulting heated polymeric material becomes elastic or super-elastic, allowing rod 52 to be readily deformed. In the illustrated embodiment, the original, molded configuration is a rod having a reduced length. Consequently, heating spinal rod 52 above the deformation temperature of the shape memory polymeric material will allow rod 52 to shorten or contract. This will urge the attached vertebrae 54, and particularly, vertebra 56, closer together. In a preferred embodiment, the internal forces causing the SMP to revert to an original, molded configuration are sufficient to urge vertebrae 54 and 56 closer together. In other embodiments, external force may be applied to urge vertebrae 54 and 56 closer together. Once the two vertebrae 54 and 56 are aligned as desired, they can be restrained or maintained in that orientation using spinal rod 52.

It will be understood by those skilled in the art that alternative embodiments of the above-mentioned procedure can be envisioned. It may be desirable to separate vertebrae or increase the disc space height between a selected pair or plurality of vertebrae. For example, a spinal rod such as that illustrated as 52 can be implanted and attached as a deformed rod that is shorter than its original, molded configuration. During surgery, after implantation, the implanted spinal rod can then be heated above the deformation temperature of the shape memory polymeric material. In the absence of any externally applied force, the implanted spinal rod will then revert to its original, molded configuration, which is longer than the implanted or first configuration. This will urge the attached vertebrae further apart and will increase the disc space height between the attached vertebrae.

Spinal rod 52 can be used in conjunction with a disc prosthesis, nucleus prosthesis, a variety of spinal implants including PLIF- or ALIF-type implants, fusion, arthrodesis, correction of improper curvature of the spine, and strengthening and support of the spine.

Additionally, it can be envisioned that one or more implanted spinal rods can be used to correct improper curvature of the spine. Such curvature is found in scoliosis, incorrect lordosis, kyphosis, and/or as a result of trauma. In preferred embodiments, a pair of spinal rods positioned around or opposite each other on the vertebral bodies can be used. For example, one implant can be provided on one lateral side of the spinal column. A second implant can be provided on the opposite, lateral side of the spinal column. The first spinal rod can be used to decrease the disc space height between the attached vertebrae; the corresponding, opposite spinal rod can be used to increase the disc space height between the attached vertebrae. The combination of the two attached spinal rods can then be used to correct a spinal curvature or deformity.

Figure 3:
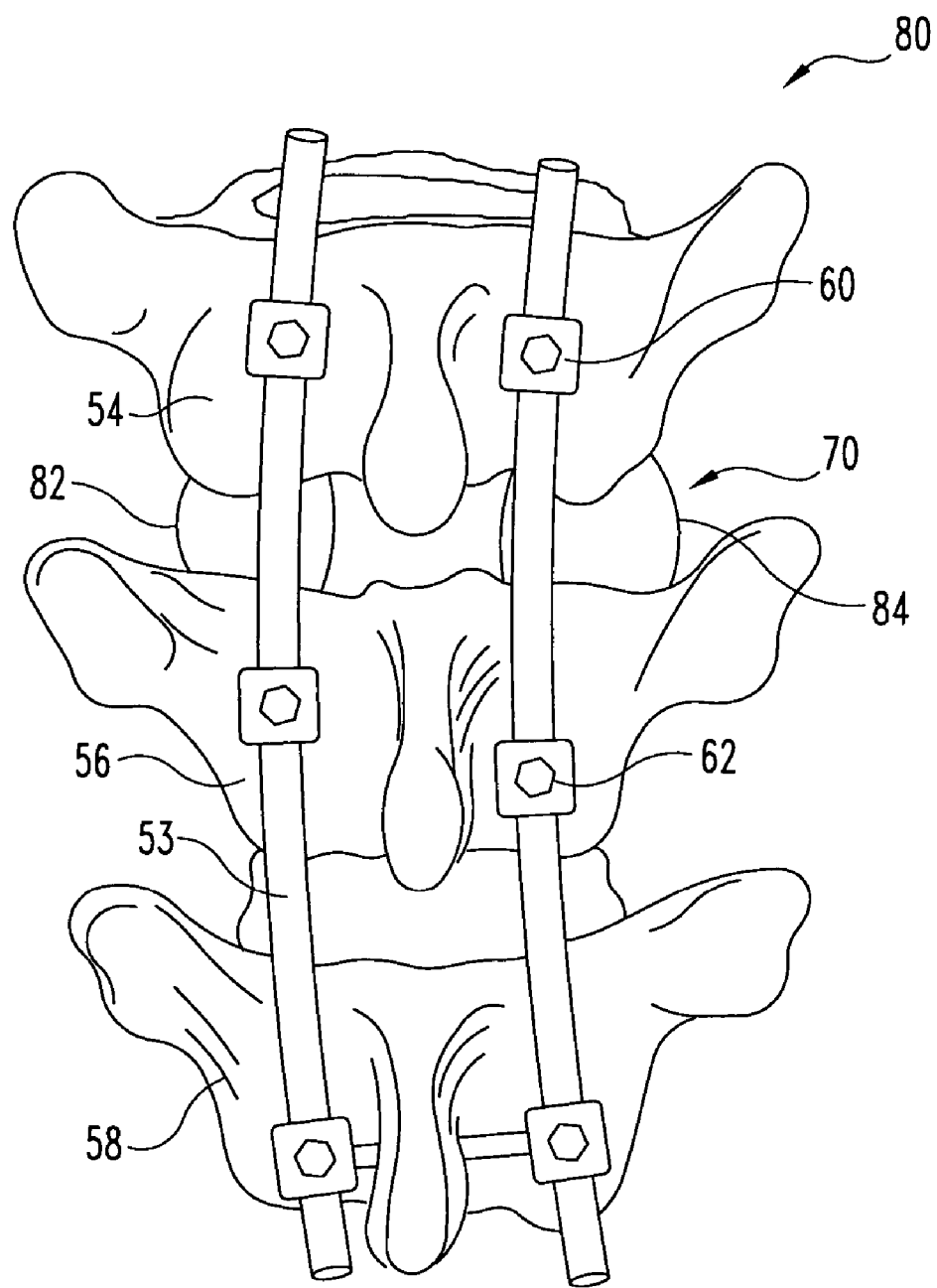
FIG. 3 is a plan view of yet another embodiment of a pair of spinal rods formed of a shape memory polymeric material in accordance with the present invention.

FIG. 3 illustrates assembly 80 including a spinal rod 82 derived from spinal rod 52 and spinal rod 83 derived from spinal rod 53. Assembly 80 is formed similarly to assembly 50 and like reference numbers will be used to denote like components. As noted, spinal rod 82 is derived from spinal rod 52 albeit in a reduced length configuration. In this embodiment, spinal rod 82 is provided to resemble or approximate the original, molded configuration. It can be observed that original disc space 70 has been significantly reduced in height. Additionally a pair of spacers 84 and 86 has been implanted into the disc space to maintain disc space height and/or promote spinal fusion. It will be understood by those skilled in the art that due to physical constraints and forces within the system, spinal rod 82 may not revert exactly to its original, molded configuration.

Additionally, it can be observed that both spinal rods 82 and 83 curve along their length. This curvature can be a result of either an applied constraint upon rods 82 and 83, which are frozen in the resulting configuration. Alternatively, the curvature exhibited by rods 82 and 83 can be an approximation of their molded, original configuration.

Figure 4:
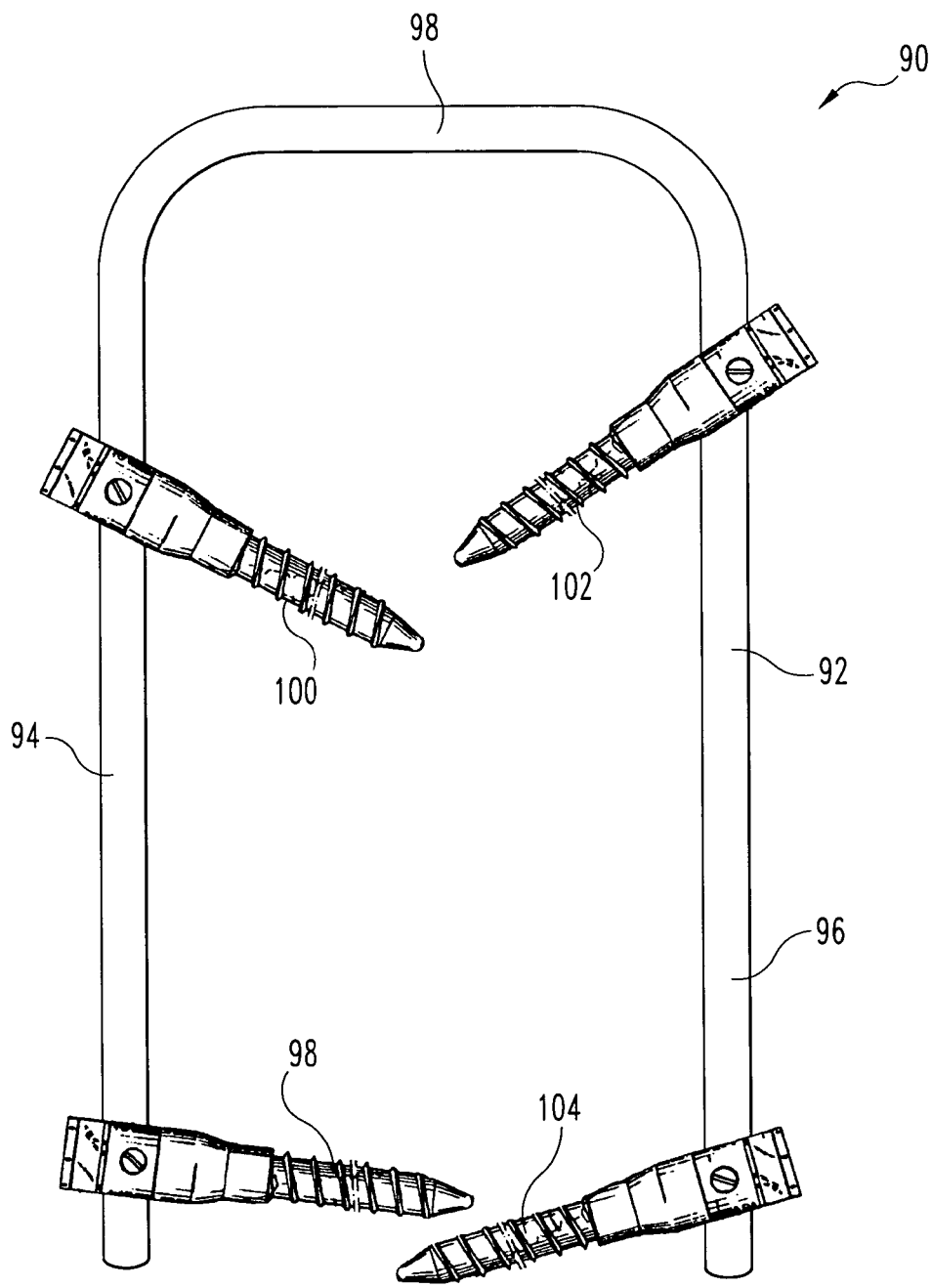
FIG. 4 is a perspective view of another embodiment of a spinal rod in accordance with the present invention.

FIG. 4 illustrates yet another embodiment of a spinal rod assembly 90. Assembly 90 includes a spinal rod 92 formed in the shape of an inverted "U". In this configuration, spinal rod 92 includes a first leg portion 94 and an opposite, substantially parallel second leg portion 96. A transverse portion 98 interconnects leg portion 94 with leg portion 96. Transverse portion 98 is illustrated as a straight rod interconnecting the two leg portions 94 and 96. It is to be understood that transverse portion 98 can be shaped and/or configured as desired. For example, transverse portion 98 can exhibit an inverse "V" or a curved configuration. In use, spinal rod 92 can be fitted onto two or more vertebrae. For example, spinal rod 92 can be provided such that a first leg portion 94 extends up or down the posterior portion of a pair of adjacent vertebrae. The transverse section 98 could then extend laterally over the spinous process of a selected vertebra, for example, a lumbar vertebra. Additionally, assembly 90 includes two or more bone fasteners illustrated in FIG. 4 as pedicle screws 98, 100, 102, and 104. It will be understood by those skilled in the art that spinal rod 92 can include fewer than four pedicle screws or more than four pedicle screws. Furthermore, the bone fasteners for use with spinal rod 92 need not include a pedicle screw, but spinal rod 92 can be attached to a selected bone portion using glue, staples, wires, nails, bone screws, bone hooks, and the like.

Rod 92 comprises an SMP material. Consequently, rod 92 can be deformed similarly to rod 12. Additionally, rod 92 can be further deformed such as by splaying leg portions 94 and 96, independently introducing one or more bends or curves into either leg portion 94 or 96, or by lengthening/compressing either or both leg portions 94 and 96. Other deformation will become apparent from a skilled surgeon or orthopedic specialist when presented with a particular bone defect. Each deformation is intended to be included within the scope of the present invention.

Figure 5:
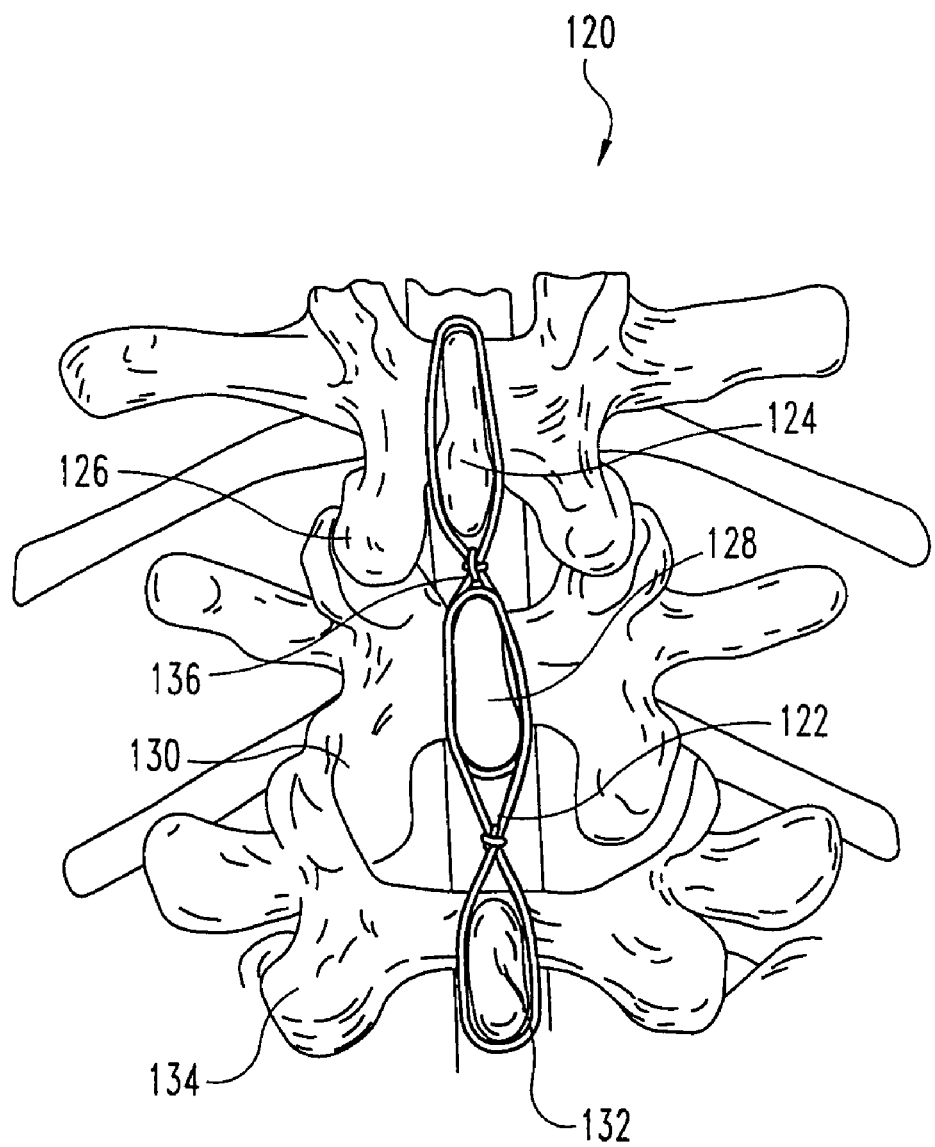
FIG. 5 is one embodiment of a tension band attached to a series of vertebral bodies to promote spinal fixation in accordance with the present invention.

FIG. 5 illustrates yet another embodiment of a bone fixation assembly 120. Bone assembly 120 is illustrated to include cord 122 formed in the shape of a wire or braid and comprising a shape memory polymeric material. Assembly 120 can include either a single cord 122 or a plurality of cords which may or may not be braided or twisted together. Cord 122 is illustrated wrapped around the spinous process 124 of vertebral body 126. Cord 122 then extends to and wraps around spinous process 128 of vertebral body 130. In the illustrated embodiment, cord 122 is illustrated as wrapping around spinous process 128 in a plurality of loops. It should be understood that in alternative embodiments, cord 122 need not completely encircle spinous process 128. In other alternative embodiments, cord 122 can be secured to vertebral body 128 through a variety of known fasteners, including glue, staples, nails, bone screws, bone hooks, and the like. From spinous process 128, cord 122 then continues to spinous process 132 of vertebral body 134. Cord 122 completely encircles spinous process 132 in at least a plurality of loops. As also noted above, it will be understood by those skilled in the art that cord 122 need not be secured to spinous process 132, but rather cord 122 can be secured to vertebral body 134 in a variety of known manners. It should also be understood by those skilled in the art that cord 122 need not interconnect three vertebrae. Cord 122 can connect two adjacent vertebrae or four or more vertebrae. Once cord 122 has been used to interconnect the desired number of vertebrae in the desired fashion, cord 122 can be secured either to itself using a knot 136 or can be secured to one or more vertebrae 126, 130, and 134. Once the desired number of vertebral bodies have been interconnected using cord 122, the shape memory polymeric material can be heated above $T_d$, allowing it to become elastic or super-elastic. In the absence of any counteractive force, the shape memory polymeric material will induce the cord 122 to revert to its original, molded configuration. In one preferred embodiment, the original, molded configuration has a reduced length. In this embodiment, heating cord 122 above its deformation temperature will induce it to shorten its length and thereby urge the attached vertebrae together. This will in effect reduce the disc space height between the attached vertebrae.

The assemblies 80 and/or 120 as disclosed in the present invention include bone fasteners and interconnection elements. The bone fasteners fix or secure portions or rods of an assembly to bony tissue. The interconnection elements interconnect two or more rods together. It is intended to include within the meaning of the term interconnection elements a variety of connectors, bone fasteners such as pedicle screws, other bone screws, bone hooks, transverse connectors, and the like.

Figure 6:
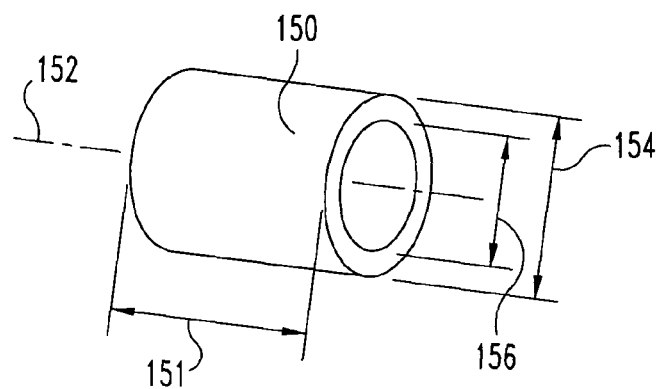
FIG. 6 is a perspective view of one embodiment of a cylindrical collar for use in a connector in accordance with the present invention.

FIG. 6 illustrates a collar for use in a bone fastener or interconnection element in accordance with the present invention. Collar 150 is formed of a shape memory polymeric material. Collar 150 can be sized and configured to engage a rod such as rods 12, 16, 17, 30, 52, 53, 82, 83 and 92 described above. In the illustrated embodiment, collar 150 is provided in its original, molded configuration. The original, molded configuration exhibits a pre-determined length represented by reference line 151 extending along longitudinal axis 152. Additionally, the original, molded configuration has a pre-determined outer diameter illustrated by reference 154 and/or a pre-determined inner diameter indicated by reference 156. In a preferred embodiment, the length of collar 150 measured along its longitudinal axis is between about 3 mm and about 12 mm; more preferably between about 5 mm and about 10 mm. In other embodiments, the outer diameter of collar 150 is provided to be between 4mm and 10 mm; more preferably between about 5 mm and about 8 mm. In still yet other embodiments, collar 150 is provided to have an inner diameter indicated by reference 156 between about 3 mm and about 8 mm; more preferably between about 4 mm and about 7 mm.

Figure 7:
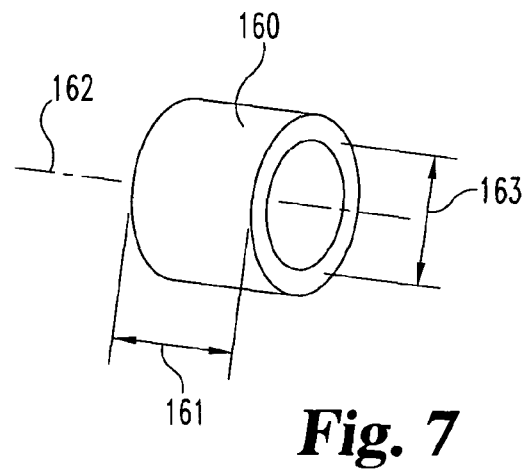
FIG. 7 is a perspective view of one embodiment of a deformed collar derived from the collar illustrated in FIG. 6.

FIG. 7 illustrates collar 160 derived from collar 150. Collar 160 is provided in a first configuration deformed from that illustrated in FIG. 6. Collar 160 is provided to have a greater inner diameter illustrated by reference 163. Collar 160 can be formed by heating collar 150 above its deformation temperature, thus allowing the shape memory polymeric material to become elastic or super-elastic. Once heated, collar 160 can be forced onto a mandrel to increase the inner diameter. Alternatively, collar 160 can be deformed to have a length represented by reference line 161 measured along longitudinal axis 162 that differs from the length of collar 150. Cooling the thus-deformed collar below the deformation temperature effectively freezes the shape memory polymeric material, thus preventing further deformation of the collar.

Figure 8:
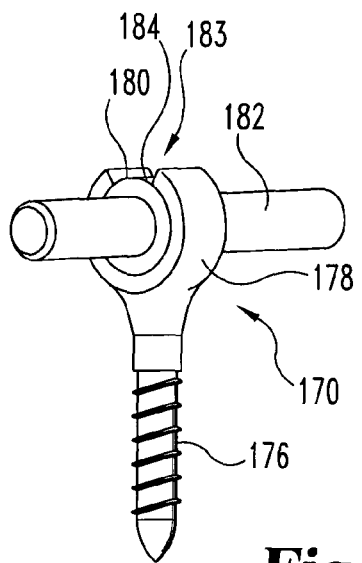
FIG. 8 is a perspective view of a spinal rod connector including a collar formed of a shape memory polymeric material interconnecting a spinal rod and a bone fastener in accordance with the present invention.

FIG. 8 is a perspective view illustrating one embodiment of a bone fastener assembly 170. Assembly 170 includes a pedicle screw 176 having a head 178 with a recess 180 formed therein. Recess 180 is illustrated as a groove in head 178. A rod 182 and collar 184 are disposed in recess 180. Rod 182 can be a spinal rod, such as 12, 16, 17, 52, 53, 82, 83 and 92, or a connecting member 30. In one embodiment, the rod 182 with collar 184 can be "top loaded" into recess 180. In this embodiment, opening 183 into recess 180 is sufficient to allow at least rod 182 to pass therethrough to rest in recess 180.

Figure 9:
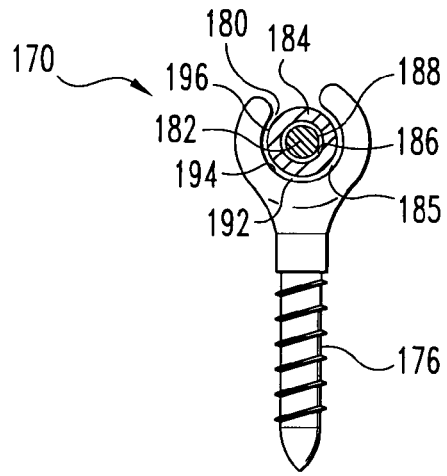
FIG. 9 is a partial cross-sectional view of the connector illustrated in FIG. 8 with the collar provided in a first, deformed configuration in accordance with the present invention.

Referring additionally to FIG. 9, which is a cross-sectional view of a fastener assembly 170, collar 184 encircles rod 182. It can be seen from the illustrated embodiment that collar 184 loosely encircles rod 182. Consequently, a space 185 exists between the inner surface 186 of collar 184 and the outer surface 188 of rod 182. This allows rod 182 to move or slide relatively freely within the interior of collar 184 and recess 180. Additionally, or in the alternative, collar 184 is sized and disposed within recess 180 to allow a space 192 to exist between the inner surface 194 of recess 180 and the outer surface 196 of collar 184. In an alternative embodiment, visibly observable spaces 185 and/or 192 need not exist. Inner surface 186 of collar 184 can contact the outer surface 188 of rod 182. In this embodiment, the contact between surfaces 186 and 188 is not constrained so that rod 182 can move or have limited slippage either rotationally or longitudinally within the interior of collar 184. Limited movement of rod 182 within the interior of collar 184 and recess 180 provides advantages. A surgeon or manufacturer can at least partly assemble the pedicle screw 176, collar 184, and rod 182. Frictional engagement of collar 184 with rod 182 and screw head 178 would be sufficient to inhibit the assembly from becoming disengaged during an operation yet still allow the surgeon the ability to adjust the orientation and disposition of rod 182 within recess 180 to achieve a desired alignment and/or treatment.

Figure 10:
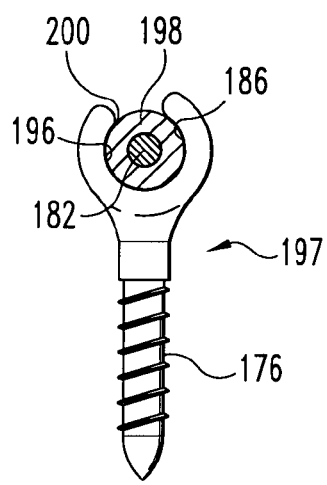
FIG. 10 is a partial cross-sectional view of the connector illustrated in FIG. 8 with the collar provided in a second, deformed configuration in accordance with the present invention.

FIG. 10 is a cross-sectional view of a bone fastener assembly 196 in which the components are rigidly interconnected. Fastener assembly 197 is formed similarly to fastener assembly 170, and the same reference numbers are used to denote the identical or substantially identical components. In this embodiment, deformed collar 198 is provided in a second configuration. In the second configuration, collar 198 engages an enclosed spinal rod 182. Additionally, the outer surface 200 of collar 198 bears against the inner surface 196 of the recess 180. In this configuration, collar 198 secures rod 182 to pedicle screw 176. Consequently, rod 182 is securely locked in place and cannot be removed, rotated, or longitudinally displaced from pedicle screw 176.

Figure 11:
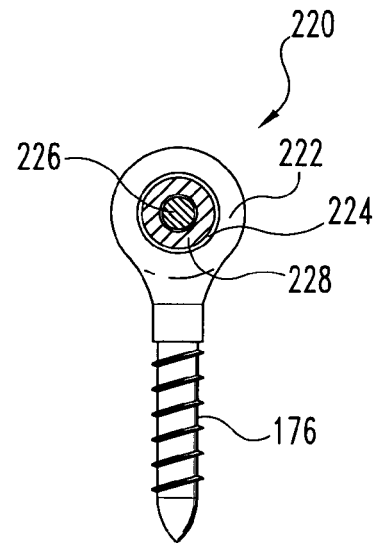
FIG. 11 is a partial cross-sectional view of another embodiment of a closed connector in accordance with the present invention.

Use of the fastener assemblies 180/197 in accordance with the present invention allows the surgeon to readily and relatively easily assemble an orthopedic support for a patient. The surgeon can then align the affected vertebrae into a desired configuration or alignment. Once the vertebrae have been aligned as desired, the surgeon then heats collar 184 above the deformation temperature of the SMP material. Above this temperature, the SMP material becomes elastic or super-elastic and is readily deformed. In a preferred embodiment, collar 184 reverts to its original, molded configuration or an approximation thereof as illustrated in FIGS. 6 and 10. In the original, molded configuration, collar 198 is sized and shaped to snugly fit within the head 178 of pedicle screw 176 and about rod 182. This effectively inhibits movement of rod 182 in the head 178 of pedicle screw 176. FIG. 11 is a partial cross-sectional view of a connector 220 with a head 222 having a recess 224 formed therein. In this embodiment, recess 224 is provided as an opening extending through head 222. Consequently, head 222 can be considered to fully encircle an included rod 226 and collar 228. Collar 228 can be provided substantially as described for collar 150.

While collars 150 and 228 are illustrated as combined with a pedicle screw, it will be understood by those skilled in the art that a collar such as that illustrated in FIG. 6 can be used with connecting elements such as connector 18 of FIG. 1. Such interconnecting rods are known in the art; for example, as illustrated in U.S. Pat. Nos. 6,296,643, 6,077,268, 5,716,355, and 5,980,523.

Each of the spacers discussed above can be formed of a material that comprises a shape memory polymer. The shape memory polymeric can be selected from a wide variety of polymers, including biodegradable and non-biodegradable polymers. In preferred embodiments, the shape memory polymeric material is formed from oligomers, homopolymers, copolymers, and polymer blends that include polymerized monomers derived from l, d, or d/l lactide (lactic acid); glycolide (glycolic acid); ethers; olefins, such as ethylene, propylene, butene-1, pentene-1, hexene-1, 4-methylpentene-1, styrene, norbornene and the like; butadiene; polyfunctional monomers such as acrylate, methacrylate, methyl methacrylate; esters, for example, caprolactone; and mixtures of these monomeric repeating units.

Use of the term copolymers is intended to include within the scope of the invention polymers formed of two or more unique monomeric repeating units. Such copolymers can include random copolymers; graft copolymers; block copolymers; radial block, diblock, and triblock copolymers; alternating copolymers; and periodic copolymers. Use of the term polymer blend is intended to include polymer alloys, semi-interpenetrating polymer networks (SIPN), and interpenetrating polymer networks (IPN).

Preferred shape-memory molded implants of this invention are fabricated to include homopolymers, copolymers, polymer blends, and oligomers of d, l, d/l, polylactide; polyglycolide, poly(lactide-co-glycolide), poly(β-hydroxy butyrate); poly(β-hydroxy butyrate-co-hydroxyvalerate), poly(trimethylene carbonate) polyurethane, poly(ethylene-co-vinyl acetate) (EVA), poly(ethylene-co-propylene) (EPR), poly(ethylene-co-propylene-co-diene) a ter-polymer (EPDM), poly(ε-caprolactone), polyimino carbonates, polyanhydrides, copolymers of ethylene and propylene and/or other α-olefins: or copolymers of these α-olefins. Among them, various types of polyethylene, such as low-density polyethylene, linear low-density polyethylene, medium-density polyethylene and high-density polyethylene, and polypropylene are preferable.

Preferred polymers include biodegradable homopolymers of lactide or glycolide or copolymers thereof. Exemplary polymers are described in U.S. Pat. No. 4,950,258, the entire disclosure of which is incorporated by reference herein. When copolymers of lactide and glycolide are used to form the spacers, the copolymers preferably consist essentially of a composition of 90-10 mol % lactide and 10-90 mol % glycolide, and most preferably consist essentially of 80-20 mol % lactide and 20-80 mol % of glycolide. Within these specified ranges, the copolymers exhibit desirable deformation characteristics. For example, the copolymers are more pliable and readily deformable at lower temperatures when their mole ratio of lactide and glycolide approximates to 1:1. Generally, the less crystalline phases in the SMP material, the lower the deformation temperature.

The polymer composition of the present invention may further contain thermoplastic resins and/or thermoplastic elastomers to improve its stiffness, moldability, and formability. In addition, the shape-memory polymeric may additionally include additives such as coloring agents, stabilizers, fillers, and the like, in an amount such as will not alter the desired shape memory effect, biocompatibility, and/or biodegradability properties of the molded components.

The polymer is characterized in that it will attempt to assume its memory condition by activation of a polymer transition. Activation can occur by basically three different mechanisms: 1) adsorption of heat or energy in whatever form by the polymer, 2) adsorption of liquid by the polymer, and 3) a change in pH in the liquid in contact with the polymer. The polymer is formulated to be responsive to adsorption of a liquid by incorporating in the polymer a hydrophilic material, such an n-vinyl pyrrolidone. Incorporation of a material such as methacrylic acid or acrylic acid into the polymer results in a polymer having a transition that is sensitive to pH. The polymer transition may be a thermally-activated transition, where upon adsorption of energy or heat the polymer undergoes a glass transition or a crystalline melting point.

As mentioned above, the SMP can be deformed by absorbing heat or energy to raise the temperature level of the SMP. The deformation temperature ($T_d$) in most materials will be substantially equal to its glass transition temperature ($T_g$). When heated above the deformation temperature, the polymeric material exhibits a elasticity or super-elasticity that allows it to be molded into a variety of shapes. For example, for the present invention, the molded components can be heated to a temperature between about 40° and about 100° C. Application of a compressive force to deform the component into a deformed configuration having a reduced length can then be applied. Preferred examples of the compressive force needed to deform the molded component are in a range between about 18 KPa and about 900 KPa. The deformed component can then be cooled below the $T_d$, which effectively freezes the component into its deformed configuration. The deformed component can be used immediately, stored for use at a later time, or used in an assembly such as a bone fastener and then either stored or shipped to the consumer. Obviously, prior to use the deformed component should be sterilized, preferably using chemical or radiation sterilization techniques.

In vivo, thermal activation of the SMP can be accomplished by a variety of techniques and instrumentation. For example, warm saline solution can be flushed over the component/SMP material. The saline can then be suctioned out of the patient. Obviously, it is preferable that the warm saline solution be kept at a low enough temperature that it does not traumatize or damage the adjacent tissue.

In yet another embodiment, a heating tool or other suitable electronic device can be used to heat the SMP without warming and traumatizing the adjacent body tissue. Suitable heat generating apparatus include a hot air gun, a small welding or soldering gun, or an electrocauter tip. Lasers, which are commonly provided in operating rooms, are also suitable. Lasers are especially desirable because they are precise and controlled in their application, can generate sufficient heat very quickly, and cause less thermal necrosis because there is less misdirected heat. The heating operation can be performed during surgery, in the body. Still other embodiments include the use of ultra sonic devices, light, and/or other electromagnetic radiation generating devices.

After the SMP has been heated above its deformation temperature, it automatically undergoes a transition in which it reverts back to its originally molded configuration. However, as has been discussed above, due to spatial constraints and/or biomechanical forces, the SMP may not be able to revert exactly to its original, molded configuration and/or dimensions. Furthermore, the surgeon may desire to at least temporarily constrain the spinal column in a desired orientation and/or alignment using external or internal instruments such as distractors and compressors. This may be required while the SMP is warm, i.e., at a temperature level approximately equal to or above its $T_d$. At this temperature range, the SMP is sufficiently plastic that the bone structures and other components of the described assemblies are not rigidly constrained. However, once the SMP has cooled to a temperature level sufficiently lower than $T_d$, the SMP is rigid. Consequently, the bony structures, molded components, and/or assemblies are rigidly constrained. Preferably, the implants, connectors, rods, and collars formed of the SMP according to this invention can be used to rigidly constrain bony structures, although less rigidly constrained than components using a metal-on-metal interconnection. Thus components formed of SMP materials provide particular advantages including reducing the risk of stress shielding new bone ingrowth.

After the component(s) are frozen into their expanded configuration, the surgeon can reduce any distraction or restriction that has been applied to the bone structure. In this expanded confirmation, the implants have sufficient compressive modulus to withstand the biomechanical load exerted by the spinal column.

To further increase the compressive modulus of the SMP, the polymeric material can include a wide variety of additives such as fillers; binders; reinforcement phases such as fibers, for example, glass fiber and carbon fibers and the like; aggregates, for example, ceramic particles or bone derived particles; and platelets to increase the compressive modules of the polymeric material.

The rods, collars, connecting elements, and fasteners of the present invention can be fabricated by a wide variety of techniques, including injection molding, extrusion molding, vacuum molding, blow molding, and transfer molding.

The present invention contemplates modifications as would occur to those skilled in the art. All publications, patents, and patent applications cited in this specification are herein incorporated by reference as if each individual publication, patent, or patent application was specifically and individually indicated to be incorporated by reference and set forth in its entirety herein.

Unless specifically identified to the contrary, all terms used herein are used to include their normal and customary terminology.

Further, while various embodiments of implants having specific components and structures are described and illustrated herein, it is to be understood that any selected embodiment can include one or more of the specific components and/or structures described for another embodiment where possible.

Further, any theory of operation, proof, or finding stated herein is meant to further enhance understanding of the present invention and is not intended to make the scope of the present invention dependent upon such theory, proof, or finding.

While the invention has been illustrated and described in detail in the drawings and foregoing description, the same is considered to be illustrative and not restrictive in character, it is understood that only the preferred embodiments have been shown and described and that all changes and modifications that come within the spirit of the invention are desired to be protected.

What is claimed is:

1. A system for treating a spinal defect said system, comprising:
    a rod member including an elongate body provided in a first configuration sufficient to extend from a first vertebra to a second vertebra, said elongate body formed of a shape memory polymeric material;
    a first fixation device connected to the rod member; and
    a second fixation device connected to the rod member and spaced axially from the first fixation device, whereby the elongate body upon absorption of thermal energy deforms to a second configuration different from the first configuration; and
    wherein each of the fixation devices comprises a bone anchor portion adapted to be anchored to vertebral bone and a head having a recess formed therein and a collar comprising a cylindrical sleeve extending along a longitudinal axis and having concentric inner and outer circular surfaces extending about the longitudinal axis, the cylindrical sleeve positioned within the recess in the head and configured to at least partially encircle the rod member with the rod member positioned within the cylindrical sleeve and extending along the longitudinal axis; and
    wherein the collar is formed of a shape memory polymeric material and having a first configuration that allows movement of the rod member relative to the fixation device, the collar being transitioned to a second configuration upon absorption of thermal energy that inhibits movement of the rod member relative to the fixation device.

2. The system of claim 1 wherein the rod member is formed of a first shape memory polymeric material and the collar is formed of a second shape memory polymeric material different from the first shape memory polymeric material.

3. The system of claim 1 comprising a second rod member.

4. The system of claim 3 further comprising a lateral connector having first and second ends respectively secured to the rod members.

5. The system of claim 4 wherein the lateral connector is formed of a shape memory polymeric material.

6. The system of claim 1 wherein the recess in the head defines a circular inner surface extending about the longitudinal axis of the cylindrical sleeve.

7. The system of claim 6 wherein the circular inner surface of the recess extends concentrically about the inner and outer circular surfaces of the cylindrical sleeve.

8. The system of claim 1 wherein rod member and the recess in the head each have a circular configuration; and
    wherein the rod member is positioned concentrically within the cylindrical sleeve and the cylindrical sleeve is positioned concentrically within the recess.

9. The system of claim 1 wherein the recess in the head is circular; and
    wherein the cylindrical sleeve and the circular recess in the head each extend concentrically about the longitudinal axis.

10. The system of claim 1 wherein the rod member, the cylindrical sleeve and the recess in the head each extend commonly along the longitudinal axis.

11. The system of claim 1 wherein the head fully encircles the rod member and the cylindrical sleeve.

12. The system of claim 1 wherein the inner circular surface of the cylindrical sleeve has a first inner diameter in the first configuration that is loosely engaged about the rod member to allow movement of the rod member within the cylindrical sleeve, the inner circular surface of the cylindrical sleeve having a second inner diameter in the second configuration that is smaller than the first inner diameter and which is compressed about the rod member in the second configuration to securely engage the cylindrical sleeve about the rod member to inhibit relative movement of the rod member within the cylindrical sleeve.

13. The system of claim 12 wherein the outer circular surface of the cylindrical sleeve has a first outer diameter in the first configuration that is loosely engaged within the recess in the head to allow relative movement of the cylindrical sleeve within the recess, the outer circular surface of the cylindrical sleeve having a second outer diameter in the second configuration that is larger than the first outer diameter and which bears against an inner surface of the recess in the second configuration to securely engage the cylindrical sleeve within the recess to inhibit relative movement of the cylindrical sleeve within the recess.

14. The system of claim 1 wherein the outer circular surface of the cylindrical sleeve has a first outer diameter in the first configuration that is loosely engaged within the recess in the head to allow relative movement of the cylindrical sleeve within the recess, the outer circular surface of the cylindrical sleeve having a second outer diameter in the second configuration that is larger than the first outer diameter and which bears against an inner surface of the recess in the second configuration to securely engage the cylindrical sleeve within the recess to inhibit relative movement of the cylindrical sleeve within the recess.

15. The system of claim 1 wherein the cylindrical sleeve has a first length along the longitudinal axis in the first configuration and a second length along the longitudinal axis in the second configuration that is different from the first length.

16. A system for treating a spinal defect said system, comprising:
a rod member including an elongate body provided in a first configuration sufficient to extend from a first vertebra to a second vertebra, said elongate body formed of a shape memory polymeric material;
a first fixation device connected to the rod member; and
a second fixation device connected to the rod member and spaced axially from the first fixation device, whereby the elongate body upon absorption of thermal energy deforms to a second configuration different from the first configuration; and
wherein each of the fixation devices comprises a bone anchor portion adapted to be anchored to vertebral bone and a head having a recess formed therein and a collar positioned within the recess in the head and configured to at least partially encircle the rod member; and
wherein the collar is formed of a shape memory polymeric material and having a first configuration that allows movement of the rod member relative to the fixation device, the collar being transitioned to a second configuration upon absorption of thermal energy that inhibits movement of the rod member relative to the fixation device; and
a second rod member;
a lateral connector having first and second ends respectively secured to the rod members, wherein the lateral connector is formed of a shape memory polymeric material; and
a connection element interconnecting the lateral connector to the rod members, said connection element comprising a collar formed of a shape memory polymeric material.

17. A system for treating a spinal defect, comprising:
a rod member;
a fixation device including an anchor portion adapted to be anchored to vertebral bone and a connector portion defining a recess; and
a collar comprising a cylindrical sleeve extending along a longitudinal axis and having concentric inner and outer circular surfaces extending about the longitudinal axis, the cylindrical sleeve positioned within the recess and at least partially encircling the rod member with the rod member positioned within the cylindrical sleeve and extending along the longitudinal axis; and
wherein at least one of the connector portion and the collar is formed of a shape memory polymeric material having a first configuration that is transitioned to a second configuration upon absorption of thermal energy, the first configuration configured to allow relative movement between the rod member and the fixation device, the second configuration configured to inhibit relative movement between the rod member and the fixation device.

18. The system of claim 17 wherein the collar is formed of the shape memory polymeric material and has a first shape that is transitioned to a second shape upon the absorption of thermal energy, the first shape being loosely engaged about the rod member to allow movement of the rod member within the collar, the second shape being securely engaged about the rod member to inhibit movement of the rod member within the collar.

19. The system of claim 18 wherein the second shape of the collar is securely engaged within the recess in the connector portion to inhibit relative movement between the rod member and the fixation device.

20. The system of claim 19 wherein the first shape of the collar is loosely engaged within the recess in the connector portion to allow relative movement of the collar within the recess.

21. The system of claim 17 wherein the rod member is formed a shape memory polymeric material, the rod member having an initial configuration that is transitioned to a different configuration upon absorption of thermal energy.

22. The system of claim 21 wherein the initial configuration of the rod member has a first length and the different configuration has a second length shorter than the first length.

23. The system of claim 21 wherein the initial configuration of the rod member has a first length and the different configuration has a second length longer than the first length.

24. The system of claim 21 wherein the initial configuration of the rod member is bent and the different configuration is substantially straight.

25. The system of claim 21 wherein the initial configuration of the rod member is substantially straight and the different configuration is bent.

26. The system of claim 17 wherein the connector portion has an open top in communication with the recess to allow the rod member to be top loaded into the recess.

27. The system of claim 17 wherein the recess in the connector portion defines a circular inner surface extending about the longitudinal axis of the cylindrical sleeve.

28. The system of claim 27 wherein the circular inner surface of the recess extends concentrically about the inner and outer circular surfaces of the cylindrical sleeve.

29. The system of claim 17 wherein rod member and the recess in the connector portion each have a circular configuration; and
wherein the rod member is positioned concentrically within the cylindrical sleeve and the cylindrical sleeve is positioned concentrically within the recess.

30. The system of claim 17 wherein the recess in the connector portion is circular; and
wherein the cylindrical sleeve and the circular recess in the connector portion each extend concentrically about the longitudinal axis.

31. The system of claim 17 wherein the rod member, the cylindrical sleeve and the recess in the connector portion each extend commonly along the longitudinal axis.

32. The system of claim 17 wherein the connector portion fully encircles the rod member and the cylindrical sleeve.

33. The system of claim 17 wherein the inner circular surface of the cylindrical sleeve has a first inner diameter in the first configuration that is loosely engaged about the rod member to allow movement of the rod member within the cylindrical sleeve, the inner circular surface of the cylindrical sleeve having a second inner diameter in the second configuration that is smaller than the first inner diameter and which is compressed about the rod member in the second configuration to securely engage the cylindrical sleeve about the rod member to inhibit relative movement of the rod member within the cylindrical sleeve.

34. The system of claim 33 wherein the outer circular surface of the cylindrical sleeve has a first outer diameter in the first configuration that is loosely engaged within the recess in the connector portion to allow relative movement of the cylindrical sleeve within the recess, the outer circular surface of the cylindrical sleeve having a second outer diameter in the second configuration that is larger than the first outer diameter and which bears against an inner surface of the recess in the second configuration to securely engage the cylindrical sleeve within the recess to inhibit relative movement of the cylindrical sleeve within the recess.

35. The system of claim 17 wherein the outer circular surface of the cylindrical sleeve has a first outer diameter in the first configuration that is loosely engaged within the recess in the connector portion to allow relative movement of the cylindrical sleeve within the recess, the outer circular surface of the cylindrical sleeve having a second outer diameter in the second configuration that is larger than the first outer diameter and which bears against an inner surface of the recess in the second configuration to securely engage the cylindrical sleeve within the recess to inhibit relative movement of the cylindrical sleeve within the recess.

36. The system of claim 17 wherein the cylindrical sleeve has a first length along the longitudinal axis in the first configuration and a second length along the longitudinal axis in the second configuration that is different from the first length.

37. A system for treating a spinal defect, comprising:
a rod member sized to extend from a first vertebra to a second vertebra;
a first fixation device adapted to be anchored to the first vertebra; and
a second fixation device adapted to be anchored to the second vertebra; and
wherein each of the fixation devices includes a connector portion defining a recess and a collar comprising a cylindrical sleeve extending along a longitudinal axis and having concentric inner and outer circular surfaces extending about the longitudinal axis, the cylindrical sleeve positioned within the recess and at least partially encircling the rod member with the rod member positioned within the cylindrical sleeve and extending along the longitudinal axis; and
wherein at least one of the connector portion and the collar is formed of a shape memory polymeric material having a first configuration that is transitioned to a second configuration upon absorption of thermal energy, the first configuration configured to allow relative movement between the rod member and the fixation device, the second configuration configured to inhibit relative movement between the rod member and the fixation device.

38. The system of claim 37 wherein the collar is formed of the shape memory polymeric material and has a first shape that is transitioned to a second shape upon the absorption of thermal energy, the first shape being loosely engaged about the rod member to allow movement of the rod member within the collar, the second shape being securely engaged about the rod member to inhibit movement of the rod member within the collar.

39. The system of claim 38 wherein the second shape of the collar is securely engaged within the recess in the connector portion to inhibit relative movement between the rod member and the fixation device.

40. The system of claim 39 wherein the first shape of the collar is loosely engaged within the recess in the connector portion to allow relative movement of the collar within the recess.

41. The system of claim 37 wherein the recess in the connector portion defines a circular inner surface extending about the longitudinal axis of the cylindrical sleeve.

42. The system of claim 41 wherein the circular inner surface of the recess extends concentrically about the inner and outer circular surfaces of the cylindrical sleeve.

43. The system of claim 37 wherein rod member and the recess in the connector portion each have a circular configuration; and
wherein the rod member is positioned concentrically within the cylindrical sleeve and the cylindrical sleeve is positioned concentrically within the recess.

44. The system of claim 37 wherein the recess in the connector portion is circular; and
wherein the cylindrical sleeve and the circular recess in the connector portion each extend concentrically about the longitudinal axis.

45. The system of claim 37 wherein the rod member, the cylindrical sleeve and the recess in the connector portion each extend commonly along the longitudinal axis.

46. The system of claim 37 wherein the connector portion fully encircles the rod member and the cylindrical sleeve.

47. The system of claim 37 wherein the inner circular surface of the cylindrical sleeve has a first inner diameter in the first configuration that is loosely engaged about the rod member to allow movement of the rod member within the cylindrical sleeve, the inner circular surface of the cylindrical sleeve having a second inner diameter in the second configuration that is smaller than the first inner diameter and which is compressed about the rod member in the second configuration to securely engage the cylindrical sleeve about the rod member to inhibit relative movement of the rod member within the cylindrical sleeve.

48. The system of claim 47 wherein the outer circular surface of the cylindrical sleeve has a first outer diameter in the first configuration that is loosely engaged within the recess in the connector portion to allow relative movement of the cylindrical sleeve within the recess, the outer circular surface of the cylindrical sleeve having a second outer diameter in the second configuration that is larger than the first outer diameter and which bears against an inner surface of the recess in the second configuration to securely engage the cylindrical sleeve within the recess to inhibit relative movement of the cylindrical sleeve within the recess.

49. The system of claim 37 wherein the outer circular surface of the cylindrical sleeve has a first outer diameter in the first configuration that is loosely engaged within the recess in the connector portion to allow relative movement of the cylindrical sleeve within the recess, the outer circular surface of the cylindrical sleeve having a second outer diameter in the second configuration that is larger than the first outer diameter and which bears against an inner surface of the recess in the second configuration to securely engage the cylindrical sleeve within the recess to inhibit relative movement of the cylindrical sleeve within the recess.

50. The system of claim 37 wherein the cylindrical sleeve has a first length along the longitudinal axis in the first configuration and a second length along the longitudinal axis in the second configuration that is different from the first length.

* * * * *